United States Patent [19]

Witzel et al.

[11] 4,238,475
[45] Dec. 9, 1980

[54] CHEWING CUM CAPABLE OF RELEASING FINELY DIVIDED WATER-INSOLUBLE MATERIALS THEREFROM

[75] Inventors: Frank Witzel, Spring Valley; Wayne J. Puglia, Bellerose Village; K. Warren Clark, Brewster; Donald A. M. Mackay, Pleasantville, all of N.Y.

[73] Assignee: Life Savers Inc., New York, N.Y.

[21] Appl. No.: 62,861

[22] Filed: Aug. 1, 1979

[51] Int. Cl.³ .......................... A23G 3/30; A61K 9/68
[52] U.S. Cl. ......................................... 424/48; 426/3
[58] Field of Search ........................................ 426/3-6; 424/48

[56] References Cited

U.S. PATENT DOCUMENTS

| | | | |
|---|---|---|---|
| 3,011,949 | 12/1961 | Bilotti | 424/48 |
| 3,075,884 | 1/1963 | Bilotti et al. | 424/48 |
| 3,352,689 | 11/1967 | Bilotti | 426/3 |
| 3,635,735 | 1/1972 | Patil | 426/3 |
| 3,655,866 | 4/1972 | Bilotti | 426/3 |

*Primary Examiner*—Shep K. Rose
*Attorney, Agent, or Firm*—Lawrence S. Levinson; Burton Rodney

[57] ABSTRACT

A chewing gum is provided which is capable of releasing into the oral cavity relatively large amounts of finely-divided water-insoluble therapeutic materials, which chewing gum includes a water-soluble phase formed of aqueous softener, and the finely divided therapeutic component to be released, said therapeutic component being coated with a water-soluble coating agent for preventing resorption of therapeutic component back into the gum base and, optionally, a first sweetener, dispersed throughout the aqueous softener, and a relatively water-insoluble phase formed of a plurality of separate and distinct masses suspended in and dispersed throughout the water-soluble phase, each of said masses formed of particles of gum base and, optionally, particles of a second sweetener, such as mannitol and/or sorbitol or sugar, enveloped by particles of gum base. Upon chewing the above gum, the therapeutic component is, in fact, released in the oral cavity in relatively large quantities, together with the aqueous softener.

The therapeutic component to be released may comprise orally beneficial materials, such as dicalcium phosphate, antacids, such as magnesium hydroxide, calcium carbonate, as well as vitamins, drugs and the like. In a preferred embodiment, the therapeutic component is coated with gum arabic to facilitate release from chewing gum.

22 Claims, 4 Drawing Figures

CHEWING CUM CAPABLE OF RELEASING FINELY DIVIDED WATER-INSOLUBLE MATERIALS THEREFROM

FIELD OF THE INVENTION

The present invention relates to chewing gums capable of releasing finely-divided water-insoluble therapeutic materials, such as dicalcium phosphate, magnesium hydroxide, calcium carbonate, vitamins, drugs, and the like.

BACKGROUND OF THE INVENTION

U.S. Pat. No. 3,011,949 to Bilotti discloses a method for promoting release of active ingredients, such as dicalcium phosphate, chlorophyllins, powdered vitamins and antacid powders, from slab chewing gum wherein the individual solid particles of the active ingredient to be released is coated with wet sugar, dried, pulverized, and then the sugar-coated particles are mixed with the constituents which complete the slab gum formulation.

U.S. Pat. No. 3,655,866 to Bilotti discloses a sugarless gum containing a freely releasable form of dicalcium phosphate prepared by coating or agglomerating dicalcium phosphate powder with a water-soluble polyol such as mannitol, sorbitol, xylitol or arabitol.

Figure 4:
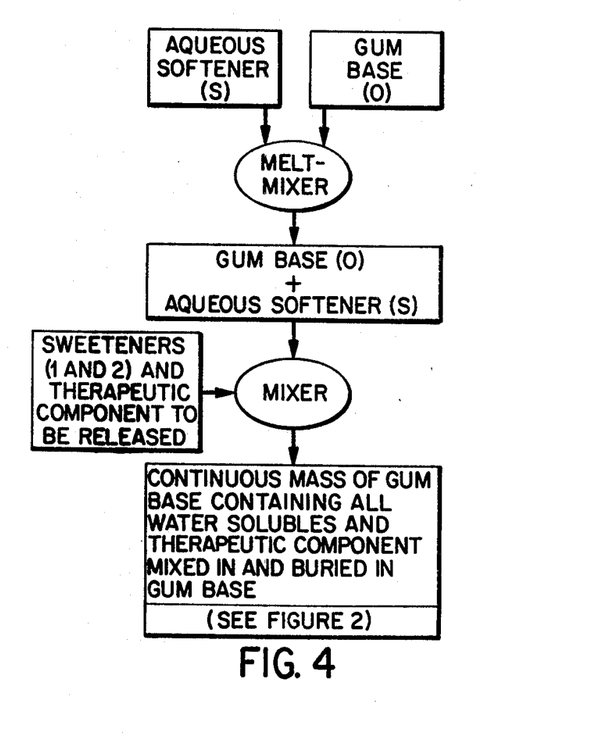
FIG. 4 is a schematic flow diagram illustrating the steps employed in making the chewing gum as shown in FIG. 2.

Conventional chewing gum generally includes gum base to which are added water-soluble sweeteners, for example, various sugars such as sucrose and dextrose, corn syrup, sorbitol and/or artificial sweeteners such as sodium or calcium saccharin, cyclamates, emulsifiers such as lecithin, mono-and diglycerides, and flavors. The chewing gum is generally prepared (as shown in FIG. 4) by melting the gum base (O), mixing corn syrup or other aqueous softener (S) for 3 to 5 minutes with the gum base followed by the addition of solid sweeteners (1) and (2), for example sugar, or sorbitol, and flavor and mixing for 5 minutes. The chewing gum is removed from the kettle, rolled and cut to the desired shape.

Figure 2:
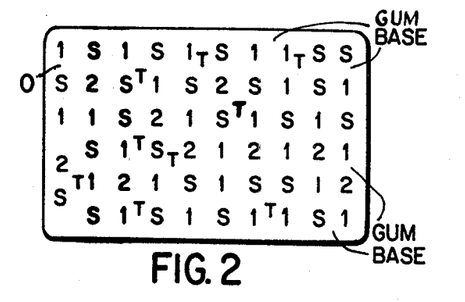
FIG. 2 is a schematic microscopic representation of a portion of a chewing gum similar in composition to the chewing gum shown in FIG. 1 prepared according to conventional methods of manufacture.

As the gum is processed as described above, it remains continuous throughout the entire procedure. The result is that the final chewing gum product is a continuous mass of gum base (O) which envelopes the sugar or other sweeteners (1) and (2) as well as the aqueous softener (S) so as to provide a matrix of gum base (O) containing sweetener (1) and (2) and aqueous softener (S) (see FIG. 2).

The gum so-produced initially provides a desirable strong sweet taste which declines rapidly during the first three to five minutes of chewing to a very slight imperceptible level of sweetness. After about five minutes or less, substantially all sweetness is gone. Accordingly, there clearly is a need for a chewing gum which possesses long-lasting sweetness, that is, sweetness which lasts for seven to eight minutes or longer. Furthermore, a need exists for a long-lasting sugarless gum which contains only natural sweeteners and no artificial sweeteners.

Where it has been attempted to prepare a chewing gum employing the above procedure containing a therapeutically active water-insoluble material, such as nystatin, it has been found that the therapeutic material is not easily released. This is so even if the therapeutic material is coated with sugar or a polyol as described in the above-described Bilotti patents.

It is generally conceded by the medical profession that small continued doses of medicaments are of greater therapeutic value than larger single doses in the practice of oral prophylaxis. Treatment of the oral cavity with bitter tasting alkaloids or antibiotics, such as nystatin, becomes a special problem because of patient rejection.

Thus, a medicament delivery system which will control the release of medicaments below the bitter taste threshold and still maintain therapeutic properties would be of great value to the medical profession. In fact, chewing gum would be ideal for such a delivery system in that the act of chewing would automatically release the medicine and at the same time prevent excessive build up in the oral cavity because of constant washing by saliva.

DETAILED DESCRIPTION OF THE INVENTION

In accordance with the present invention, it has now been found that chewing gum prepared in accordance with the technique described hereinafter, makes an excellent delivery system for certain therapeutic water-insoluble materials, such as nystatin, dicalcium phosphate, and magnesium hydroxide. The chewing gum of the invention will release and deliver certain medicaments and therapeutic water-insoluble hard to release materials in an efficient manner while inhibiting resorption of such materials back into the gum base. In the case of medicaments, such as nystatin, the chewing gum of the invention delivers the medicament in an effective therapeutic concentration, below the bitter threshold thereof, and/or in a concentration such that the sweetener present in the chewing gum masks any unpleasant taste.

Figure 1:
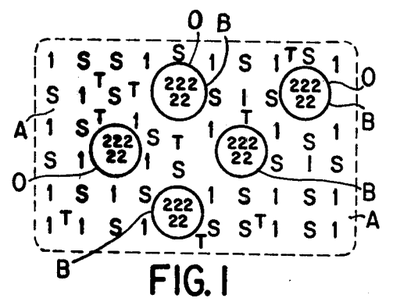
FIG. 1 is a schematic microscopic representation of a portion of the chewing gum of the invention.
Figure 3:
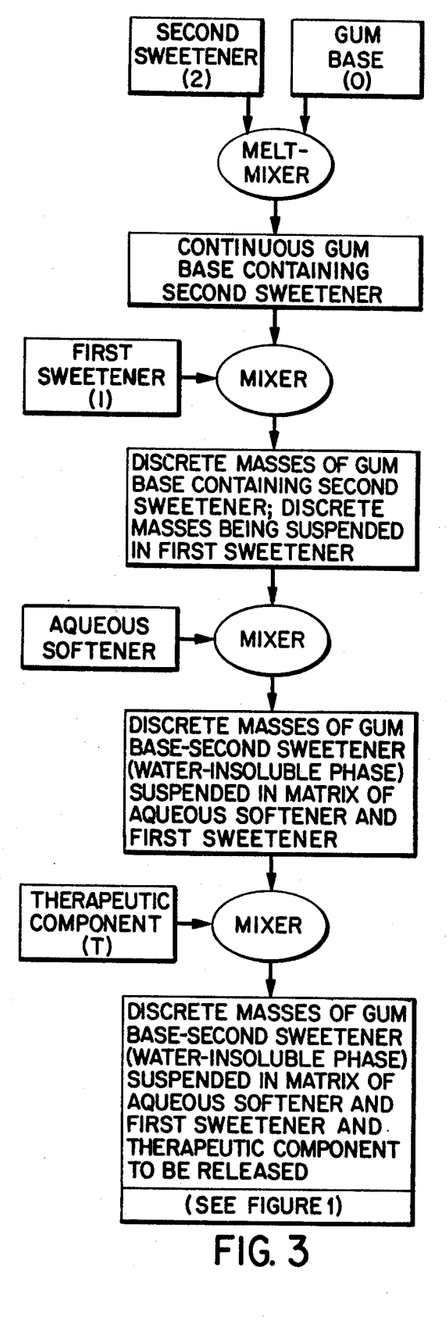
FIG. 3 is a schematic flow diagram illustrating the steps employed in making the chewing gum of the invention as shown in FIG. 1.

Referring to FIGS. 1 and 3, the chewing gum of the invention includes a water-soluble phase (A) formed of aqueous softener (S), such as sorbitol syrup, the therapeutic or active ingredient to be released (T), and optionally, a first sweetener (1), such as sorbitol or sugar, in particulate form dispersed throughout the aqueous softener (S); and a relatively water-insoluble phase (B) formed of a plurality of separate and distinct masses suspended in and dispersed throughout the water-soluble phase (A), each of said masses being formed of gum base (O) and, optionally, particles of a second sweetener (2), such as mannitol and/or sorbitol or sugar, enveloped by particles of gum base. The active ingredient (T) is released with the first sweetener (1) (where present) and aqueous softener (S) which provides the initial impact of sweetness. The gum base (O) provides an envelope or protective vehicle for the second sweetener (2) (where present) to control and slow down release of the second sweetener, thereby providing extended sweetness after any initial sweetness impact has subsided.

Thus, as seen herein, the present invention provides both sugar-containing and sugarless chewing gums which are capable of releasing finely divided water-insoluble therapeutic or active ingredients, while preventing resorption of such materials back into the chewing gum cud or bolus. In addition, in some preferred embodiments, the chewing gums of the invention have long-lasting sweetness sufficient to mask any unpleasant taste due to the release of the therapeutic material.

The chewing gum of the invention has the unique discontinuous nougat structure shown in the accompanying Figures and described in detail hereinafter which structure greatly contributes to the release of the finely divided water-insoluble ingredients.

The term "therapeutic" or "active" material refers to powdered or finely divided water-insoluble materials which are not readily released from conventional chewing gums and which are capable of delivering therapeutic effects to the oral cavity including teeth and/or mucosa, as well as to the body, in general, such as dicalcium phosphate, chlorophyllins, antacids, such as magnesium hydroxide, calcium carbonate, aluminum hydroxide, medicaments, such as nystatin and other antibiotics, especially those employed in oral prophylaxis, vitamins, cardiovascular drugs, such as propranolol and nadolol, and the like.

In a preferred embodiment of the invention, particles of therapeutic or active materials are first coated with preferably gum arabic or other resorption preventive agent, which is impervious to gum base and is not readily assimilated into gum base, before such active materials are incorporated in chewing gum. It has been found that coating such materials increases release thereof from chewing gum and prevents resorption or reabsorption of such material back into the gum bolus. Examples of such coating materials suitable for use herein include, in addition to gum arabic, dextrins, gum tragacanth, gelatin, pectins, carboxymethyl cellulose, alginates and other hydrocolloids.

The particles of therapeutic or active material may be coated by simply adding the particles to an aqueous solution of the coating agent and mixing to form a uniform suspension. The suspension may then be dried, for example, by spray drying, drum drying, freeze drying or other conventional drying technique and then pulverized, if necessary, to produce the coated particles.

It will be appreciated that any conventional particle coating technique may be employed in forming the coated materials.

As indicated, the preferred coating material to be employed is gum arabic. Sufficient gum arabic or other resorption preventive material will be employed so as to fully coat each particle of active material. Thus, from about 4 to about 1 part of active material will be employed per part of coating agent.

The coated particles (as well as uncoated particles where employed) of active material to be added to the chewing gum will preferably have an average particle size ranging from about 100 to about 300 mesh.

During chewing, the coated therapeutic agent is quickly released and prevented from resorption back into the base because of the coating's poor affinity for gum base.

The chewing gum of the invention may be provided with an initial burst of sweetness released together with the therapeutic or active ingredient by admixing an auxiliary or first sweetener, which may be a second portion of the second sweetener, and/or other sweetener, with the gum base (containing the second sweetener already dispersed therein) prior to incorporating the therapeutic or active water-insoluble ingredient in the gum. As the mixing progresses the gum base containing the second sweetener dispersed therein is torn apart into discrete masses and suspended in the first sweetener. Thereafter, plasticizer or aqueous softener in the form of a polyhydric alcohol-type syrup is admixed with the discrete masses suspended in the first sweetener, thereby imparting a unique, soft nougat-like structure which allows for a good initial burst of sweetness and flavor and excellent extended sweetness duration of up to 8 minutes or more with good sweat resistance. Finally, the therapeutic or active water-insoluble ingredient is added and dispersed in the chewing gum, and in fact, is dispersed in the water-soluble-aqueous softener phase.

The term "first sweetener" or "auxiliary sweetener", where present, as employed herein refers to the sweetener initially extracted upon chewing and which forms a water-soluble phase with the therapeutic water-insoluble material and the aqueous softener.

The term "second sweetener", where present, as employed herein refers to the sweetener which is only slowly extracted primarily after the therapeutic or active ingredient and the first sweetener have been solubilized upon chewing; the second sweetener together with the gum base forms a water-insoluble phase or a phase which is slowly released during chewing.

In preparing the chewing gum of the invention (as seen in FIG. 3), the gum base is first melted, emulsifier such as lecithin and the second sweetener (where employed) are thoroughly mixed, for at least two minutes in the melted gum base (which is maintained at a temperature preferably not exceeding 200° F.) to effect uniform distribution and seal the second sweetener in the gum base. Flavors, food acids (where desired) are added and the mixture is mixed for from 1 to 2 minutes. The mix, at this time, is a continuous cohesive means. At this stage, the auxiliary or first sweetener (where employed), preferably in particulate form, which may be another portion of the same sweetener as the second sweetener, or other sweetener, is added to the continuous mass with mixing being continued for from 1 to 5 minutes, thereby causing the continuous mass to be torn apart into discrete, separate masses of gum base containing second sweetener sealed therein said discrete masses being suspended in particles of first sweetener to form a heterogeneous mass. The aqueous plasticizer or softener is added to and mixed with the heterogeneous mass for from 1 to 5 minutes, and preferably from 1 to 3 minutes. The particulate therapeutic or active material, preferably coated with gum arabic or other coating material, is added and mixed into the chewing gum mixture. Thereafter, the solid flavor, for example, encapsulated or fixed on dextrin or gum arabic, and water-soluble acids may be added and mixed with the gum mass to form a smooth chewing gum which may be rolled, scored and cut into desired shapes.

It will be appreciated that when the therapeutic material and the aqueous plasticizer or softener are added after the mix is in discontinuous discrete masses or clumps containing second sweetener sealed therein and suspended in the auxiliary or first sweetener, substantially all water from the aqueous plasticizer, such as sorbitol syrup, will be taken up by the water-soluble particulate auxiliary or first sweetener, and the water will not be available for solubilizing the second sweetener sealed in the gum base. The second sweetener initially added to the melted gum base to form a continuous mass will be substantially buried in the gum base and protected from any solubilization (for example, due to aqueous polyol syrup) even after the gum base mix is torn into discrete masses or clumps.

The chewing gum of the invention is formulated to release up to about 75% of the dosage requirement of active material during and up to the first five to ten minutes of chewing, or about 20% to 80% of the active ingredient present in the chewing gum during such period. Of course, the amount of active material present in the chewing gum will depend upon the nature and potency of the material, the required frequency of use, and its specific release properties from the chewing gum. Thus, where the active ingredient is dicalcium phosphate, the chewing gum may contain from about 7.5 to about 10% by weight thereof; where the active ingredient is an antacid as listed above, the chewing gum may contain from about 10 to about 20% by weight thereof; where the active ingredient is a systemic drug, the chewing gum may contain from about 0.05 to about 2% by weight thereof; where the active ingredient is a drug used in oral prophylaxis, such as nystatin, the chewing gum may contain from about 0.18 to about 0.36% by weight thereof.

The presence of the first (auxiliary) sweetener and the second sweetener in the chewing gum of the invention are important in that the first sweetener with its initial burst of sweetness will mask the taste of the quantity of active ingredient released during the first 5–10 minutes of chewing, while the second sweetener with its delayed sweetness impart, will mask the taste of residual active material released after the first ten minutes.

Examples of the second sweeteners which may be employed herein and interdispersed throughout and sealed in discrete masses of gum base to provide prolonged sweetness and masking of the taste of residual active material released include, but are not limited to, one or more of the following: natural sweeteners, such as sucrose, glucose, fructose, fructose syrup, glycyrrhizin, molasses, caramel, monoammonium salt of glycyrrhizin, mono-, di- or tri-sodium salt of glycyrrhizin, mono-, di- or tri-potassium salt of glycyrrhizin, and calcium salt of glycyrrhizin; sugar alcohols, such as mannitol, sorbitol, xylitol, maltitol; artificial sweeteners, such as calcium saccharin, sodium saccharin, free acid form of saccharin, ammonium saccharin, aspartame (L-aspartyl-L-phenylalanine methyl ester), naringin dihydrochalcone, neohesperidin dihydrochalcone, cyclamic acid, sodium cyclamate, calcium cyclamate, *Dioscoreophyllum cumminsii* (Serendipity Berry), *Stevia rebaudiana* (Stevioside), *Richardella dulcifica* (Miracle Berry), or thaumatin, with sucrose, mannitol and/or sorbitol being preferred.

The first (auxiliary) sweetener employed with the aqueous softener for initial sweetness impact and to mask the taste of active material released during the first 5–10 minutes of chewing, will preferably be easily extractable from the chewing gum and may include one or more of the following: natural sweeteners, such as sugars, sugar alcohols, such as, xylitol, sorbitol, mannitol, maltitol, or mixtures thereof, or sugar containing materials, for example, monosaccharides, such as arabinose, xylose, ribose, glucose, mannose, glactose, fructose, dextrose, or sorbose or mixtures of two or more of the foregoing monosaccharides, disaccharides, such as, sucrose, for example, cane or beet sugar, lactose, maltose or cellobiose; and polysaccharides; artificial sweeteners, such as the free acid form of saccharin, calcium saccharin, ammonium saccharin, sodium saccharin, aspartame (L-aspartyl-L-phenylalanine methyl ester), naringin dihydrochalcone, neohesperidin dihydrochalcone, cyclamic acid, sodium cyclamate and calcium cyclamate, as well as other sweeteners such as *Dioscoreophyllum cumminsii* (Serendipity Berry), *Stevia rebaudiana* (Stevioside), *Richardella dulcifica* (Miracle Berry), thaumatin and the like.

The plasticizer or aqueous softener, which together with the first sweetener and active material to be released forms the so-called water-soluble phase of the chewing gum (as opposed to the oil- or water-insoluble gum base-phase which includes the second sweetener dispersed therein) will preferably take the form of a substantially non-hygroscopic material such as a polyhydric alcohol in liquid form (xylitol syrup, sorbitol syrup, maltitol syrup or hydrogenated starch hydrolysates such as disclosed in U.S. Pat. No. Re. 26,959 and U.S. Pat. No. 3,556,811).

The aqueous softener will be employed in an amount so that the gum base: softener weight ratio will be 0.3:1 or greater.

A thickener may be employed in conjunction with the aqueous softener in an amount within the range of from about 0.1% to about 20%, and preferably from about 3% to about 10% by weight of the finished chewing gum. Examples of suitable thickeners include hydrolyzed cereal solids, malto-dextrin, modified food starch, low D.E. corn syrup solids, alginates, carrageenan, xanthan gum, gelatin, carob, tragacanth, locust bean, and other water-soluble gums, and carboxymethyl cellulose.

Malto-dextrin is particularly preferred and may be used in amounts to provide a weight ratio to the aqueous softener ranging from about 2:1 to about 1:1. The addition of the above results in increased body and strength of the aqueous softener which may be necessary for efficient sheeting of the gum.

The aqueous softener or plasticizer employed herein serves as a matrix which surrounds the islands of gum base containing the second sweetener and functions as a binder for such islands of gum base-second sweetener, and the particles of therapeutic material and first sweetener. Inasmuch as the aqueous softener (or binder) lies on the gum surface (in effect coating the masses or islands of gum base), it is preferred that the hygroscopicity of the aqueous softener be as low as possible. Thus, corn syrup which is highly hygroscopic and will readily absorb moisture causing sweating problems in hot, humid climates, is to be avoided where possible. It is preferred that the aqueous softener employed herein even in sugar-based gum be sorbitol syrup.

The aqueous softener (or binder) will contain from about 65 to about 80% and preferably from about 70 to about 75% by weight solids and will be present in an amount from about 3 to about 30% and preferably from about 5 to about 25% by weight of the chewing gum depending upon the type and amount of sweetener solids present in the softener.

The amount of the gum base present will vary depending upon the configuration of the chewing gum product and the type of sweeteners present therein. The gum base should be present in quantities sufficient to make balanced formulas which produce gum which is sufficiently discontinuous to have desirable nougat-like sweetness-flavor release properties, yet at the same time sufficiently continuous to allow for processibility into desired shapes or forms.

In the case of sugar-containing chewing gum, the water-soluble phase (aqueous softener-first sweetener-active ingredient) will usually comprise from about 23 to about 80% and preferably from about 30 to about 50% by weight of the chewing gum, the water-insoluble phase (gum base-second sweetener) will comprise from about 20 to about 75% and preferably from about 30 to about 70% by weight of the chewing gum. The first sweetener (dispersed in the aqueous softener) as described above will usually be present in an amount from about 20 to about 60% and preferably from about 25 to about 35% by weight, and the second sweetener which may be sugar or other sweetener will be present in an amount within the range of from about 20 to about 45% and preferably from about 25 to about 35% by weight of the chewing gum.

In the case of sugarless chewing gums, the water-soluble phase will usually comprise from about 50 to about 92% and preferably from about 55 to about 88% by weight of the chewing gum, whereas the water-insoluble phase will comprise from about 8 to about 50% and preferably from about 12 to about 48% by weight of the chewing gum.

The first sweetener (dispersed in the aqueous softener) as described above (for example, a sugar alcohol) will be present in an amount from about 25 to about 35% and preferably from about 28 to about 32% by weight, and the second sweetener which may be a sugar alcohol or other non-sugar sweetener will be present in amount within the range of from about 15 to about 35% and preferably from about 28 to about 32% by weight of the chewing gum.

Where artificial sweeteners are employed in the chewing gum of the invention, whether it be in the water-insoluble gum base phase or in the water-soluble aqueous softener phase, the artificial sweetener will be employed in each in amounts generally used in sugarless gums depending upon the type of artificial sweetener employed. Thus, the artificial sweetener may be employed in either or both phases in amounts ranging from about 0.02 to about 1% by weight of the chewing gum product.

It has been found that by controlling gum base concentration in the chewing gum product of the invention, it is possible to optimize release properties of the active ingredient and sweetener from the chewing gum and thereby maximize the concentrations of active ingredient and sweetener in the saliva. This is accomplished by decreasing the concentration of gum base so that a short nougat-type structure is obtained. The short nougat-type structure is easily torn apart on chewing releasing large amounts of sweetener into the saliva. Thus, in accordance with the present invention, the gum base will be present in amounts ranging from about 8 to about 25% by weight of the chewing gum, and preferably from about 12 to about 20% in the case of non-stick shaped chewing gum, for example cubes, pillows, balls, blocks, and the like, which optionally may include a sugar or sugarless coating or shell.

Where an outer shell is desired, it may be applied to the chewing gum employing coating techniques well known in the art. The coating or shell may contain sucrose, corn syrup, dextrose and/or other conventional coating ingredients and may comprise from about 10 to about 20% and preferably from about 12 to about 15% by weight of the final chewing gum product. The coating not only provides additional flavor and sweetness to the chewing gum but also protects the soft gum center and improves overall shelf-life of the gum.

In the case of chewing gum having a stick configuration, because of processing considerations, larger gum base concentrations may be necessary, preferably from about 18 to about 24% by weight of the chewing gum. Thus, chewing gums in accordance with the present invention having stick configurations will not have the short nougat-type structure associated with the aforedescribed non-stick chewing gums because of the increased gum base concentrations required in such stick gums.

The unique nougat structure of the invention is especially suitable in bubble gum manufacture. The bubble gum produced in accordance with the present invention will be formed of discrete and separate masses of gum base floating or being suspended in the aqueous softener. The fact that the gum base is broken apart during manufacture destroys the elasticity of the gum base thereby reducing snapback and resiliency so that proper length and thickness stability can be maintained for processing on high speed wrapping equipment. Thus, the chewing gum of the invention allows for processing on stick equipment within extremely tight tolerances.

Preferred are the following formulations:

| Sugar-containing | | | |
|---|---|---|---|
| | | Range Parts By Weight of Chewing Gum | |
| | | Stick | Other (Blocks) |
| A. | Water-soluble phase | | |
| | Active ingredient | 0.05–10 | 0.05–10 |
| | Sorbitol syrup (% solids 68 to 72) | 3–10 | 8–12 |
| | Sugar | 28–32 | 28–32 |
| B. | Water-insoluble phase Gum base | | |
| | Bubble gum | 20–25 | 12–20 |
| | Regular | 20–25 | 12–20 |
| | Sugar | 28–32 | 28–32 |
| Sugarless | | | |
| | | Stick | Other (Blocks) |
| A. | Water-soluble phase | | |
| | Active ingredient | 0.05–10 | 0.05–10 |
| | Sorbitol | 25–35 | 25–35 |
| | Sorbitol syrup (% solids 68 to 72) | 18–30 | 18–30 |
| B. | Water-insoluble phase Gum base | | |
| | Bubble gum | 18–25 | 12–20 |
| | Regular | 18–25 | 12–20 |
| | Mannitol or sorbitol | 20–30 | 20–30 |

In preparing the second sweetener-gum base combination, it is preferred that powdered sweetener (or perhaps even liquid sweetener) be employed to expedite dispersion or dissolution in the gum base. However, larger particle sizes may be used if the mixing time is increased to effect solubilization or milling during the mixing operation. A mixing time of no less than 2 (and preferably about 3) minutes will be employed to effect a uniform distribution of the sweetener in the gum base when conventional chewing gum sigma blade mixers are used. However, this mixing time may be shortened if more efficient mixing methods are employed.

In general, the gum base is prepared by heating and blending natural gums, synthetic resins, waxes, plasticizers, etc., in a manner well known in the art. Typical examples of the ingredients found in a chewing gum base are masticatory substances of synthetic origin such as styrene-butadiene copolymer, isobutylene-isoprene copolymer, polyisobutylene, polyethylene, petroleum wax, polyvinyl acetate, as well as masticatory substances of natural origin such as rubber latex solids, chicle, crown gum, nispero, rosidinha, jelutong, pendare, perillo, niger gutta, tunu, etc. The elastomer or masticatory substance will be employed in an amount within the range of about 5 to about 15%, preferably from about 8 to about 12%, and optimally from about 9 to about 11% by weight of the gum base composition.

In addition, the gum base will preferably contain a solvent for the elastomer which should have minimal tackifying properties and will preferably comprise hydrogenated ester gum, that is, glycerol ester of hydrogenated rosin and/or dimerized ester gum.

Other conventional ingredients which may be present in the gum base include a hydrophilic-type detackifier which will sorb saliva and become slippery and is incompatible with the elastomer and solvent for the elastomer, such as polyvinyl acetate, polyvinyl butyl ether, copolymers of vinyl esters and vinyl ethers.

The gum base may also include hard waxes which serve as lubricants and should have a melting point of above about 65° C. and preferably above about 75° C. Examples of such hard waxes include candelilla wax, paraffin wax, carnauba wax, ozokerite, oricury, microcrystalline wax, and the like.

The gum base may also include a softening agent and lubricant combination which may comprise one or more hydrogenated vegetable or animal fats having a high melting point, that is above about 22° C.

The gum base will also include an emulsifier to impart hydrophilic properties to the gum base so that saliva will be absorbed thereby making the gum base slippery. Examples of such emulsifiers include glyceryl monostearate, phosphatides, such as lecithin and cephalin, Tweens, Spans and mixtures thereof.

In addition, the gum base may include colorants such as titanium dioxide, plasticizers, such as lanolin, stearic acid, sodium stearate, potassium stearate and the like, antioxidants, in an amount up to about 1000 ppm of the gum base, such as butylated hydroxytoluene, butylated hydroxyanisole, and/or propyl gallate.

The gum base may also contain particles of chalk ($CaCO_3$) as a bulking agent and texturizer in amounts ranging from about 0 to about 75%, and preferably from about 0.2 to about 25% by weight of the gum base. However, where the gum base is to be employed in a substantially calorie-free gum, the gum base may include from about 32 to about 75% and preferably from about 35 to about 70% by weight texturizing agent or inert filler. Examples of texturizing agents or inert fillers suitable for use herein include calcium carbonate, aluminum hydroxide, alumina, magnesium carbonate, talc, aluminum silicates and mixtures thereof. In addition, the gum base may be mixed with artificial sweeteners and/or food acids as set out herein to provide initial burst of sweetness or sourness and/or prolongation of sweetness.

The water-insoluble gum base may consist of any of the various bases disclosed for example in U.S. Pat. Nos. 3,052,552 and 2,197,719.

The chewing gum of the invention may include flavoring, such as sour or fruit flavoring or non-acid or mint flavoring in an amount ranging from about 0.3 to about 2.0% by weight, and preferably from about 0.5 to about 1.2% by weight of the final gum product. The flavoring may comprise oils derived from plants, leaves, flowers, fruit, etc. Representative flavor oils of this type include citrus oils such as lemon oil, orange oil, lime oil, grapefruit oil, fruit essences such as apple essence, pear essence, peach essence, strawberry essence, apricot essence, raspberry essence, cherry essence, plum essence, pineapple essence, as well as the following essential oils: peppermint oil, spearmint oil, mixtures of peppermint oil and spearmint oil, clove oil, bay oil, anise oil, eucalyptus oil, thyme oil, cedar leaf oil, cinnamon oil, oil of nutmeg, oil of sage, oil of bitter almonds, cassia oil, and methylsalicylate (oil of wintergreen). Various synthetic flavors, such as mixed fruit, may also be incorporated in the chewing gum of the invention with or without conventional preservatives. The above flavors may be added with the aqueous softener and be a part of the water-soluble phase and/or added with the second sweetener to the gum base and be a part of the so-called water-insoluble phase.

In order to provide an initial taste or sensation of sourness, the chewing gum of the invention may also contain food acid such as citric acid, tartaric acid, malic acid, and the like, in an amount ranging from about 0.3 to about 2.0% by weight, and preferably from about 0.5 to about 1.2% by weight of the final gum product. Such food acid may be added to the gum with the aqueous softener or water-soluble phase, in order to facilitate initial sourness. In addition, insoluble acids such as fumaric or encapsulated soluble acids may be added with the second sweetener and buried in the gum base in order to sustain lasting sourness.

The following Examples illustrate preferred embodiments of the invention.

EXAMPLE 1

Chewing gum containing freely releasable particles of nystatin coated with gum arabic having the composition set out below is prepared as follows.

|  | Parts by Weight |
| --- | --- |
| Gum base | 17 |
| Sugar | 66 |
| Sorbitol syrup (68-72% sorbitol solids) | 11 |
| Malto-dextrin | 4 |
| Nystatin (coated with gum arabic) | 0.2 |
| Peppermint oil | 1 |
| Yelkin (Lecithin) | 0.2 |
| Peppermint (Spray dried flavor) | 0.5 |

Particles of nystatin coated with gum arabic are prepared by simply mixing particles of nystatin (average size of 200 mesh) into a 25% aqueous solution of gum arabic to form a suspension. The suspension is spray dried to produce the nystatin particles coated with gum arabic, weight ratio nystatin:gum arabic, 75:25.

The gum base is added to a steam jacketed kettel equipped with a sigma blade mixer. The temperature of the kettle is maintained at about 180° F. to 200° F. About one half of the sugar is thoroughly mixed into the melted gum base (while the gum base is folding well) for about 3 minutes to disperse the sugar throughout the continuous mass of gum base. The sugar is thereby trapped in or otherwise protected by the gum base. The liquid flavor is added and mixed for 1 minute. The remaining sugar is added with mixing for about 2 minutes thereby causing the mass to be torn into discrete pieces. Maltrin M100 (malto-dextrin) and liquid sorbitol are added to bring the mass together and mixed for about 2 minutes. At this point discrete pieces of gum base with trapped sugar are suspended in a water soluble matrix of sorbitol liquid, malto-dextrin and sugar. Into this water soluble phase is added the nystatin sealed in gum arabic and mixed until a homogeneous dispersion is achieved.

The homogeneous dispersion is allowed to cool and is then sheeted, scored and cut into sticks (2.8 g each) and each containing 5 mg nystatin.

As a Control A, chewing gum is prepared as described above except that the nystatin present in the chewing gum is uncoated.

The Example 1 and Control A chewing gums are tested for nystatin release as follows.

Ten human subjects are asked to chew the Example 1 gum for 20 minutes, to collect all the saliva generated, and to swallow as little as possible. Microbiological assay of the samples give nystatin units of between 5 and 25 units/ml.

Upon examination of the residual nystatin contents of the chewed gums and the saliva content of the subjects, it is found that the Example 1 chewing gum released about 76% of the nystatin originally present over the 20 minute test period.

A similar test conducted with the Control A chewing gum (contains uncoated nystatin) indicates that only from 0-4% of the nystatin is released.

It is also found that the Example 1 chewing gum of the invention containing the gum arabic coated nystatin delivered the nystatin in a manner such that the bitter taste thereof is masked by the sweeteners present in the chewing gum.

Control gums B and C are prepared and tested in order to demonstrate the unique release characteristics and benefits obtained using the Example 1 chewing gum.

The Control B and C gums have the following composition and are prepared by conventional techniques as described below.

|  | Controls B and C Parts by Weight |
|---|---|
| Gum base | 22 |
| Sugar | 50 |
| Corn syrup | 17 |
| Sorbitol | 10 |
| Peppermint Oil | 1 |
| Yelkin (Lecithin) | 0.2 |
| Peppermint (Spray dried) | 0.5 |

In the Control B formulation 0.2 part of nystatin coated with gum arabic (as described above) is present, while in the Control C formulation, 0.2 part of uncoated nystatin is present.

The Control B gum is prepared as follows.

The gum base is melted and mixed with lecithin and corn syrup and the nystatin sealed in gum arabic for 5 minutes. All of the powdered sugar is added and the liquid flavor are mixed for 5 minutes. The resulting gum is cooled, sheeted, scored and cut into sticks (2.8 g each) and each containing 5 mg nystatin.

The Control C gum is prepared as described above except that uncoated nystatin is employed.

The Control B and C gums are tested by giving each of them to five human subjects who are asked to chew each 2.8 gm slab of gum for 20 minutes and to collect all of the saliva generated.

The results obtained indicate that upon chewing the Control B gum containing the gum arabic coated nystatin, about 24% of the nystatin is released during 20 minutes of chewing, while upon chewing the Control C gum containing the uncoated nystatin, 0-4% of the nystatin is released.

In view of the above results, it is clearly seen that both the unique structure of the chewing gum (Example 1) and the use of the gum arabic coating greatly contribute to the release of the nystatin from the chewing gum.

The results described above are summarized below.

TABLE I

| Example | % Released after 20 minutes of chewing |
|---|---|
| Control C Normal structure Nystatin (not coated) | 0-4% |
| Control A Nougat structure Nystatin (not coated) | 0-4% |
| Control B Normal structure Nystatin (coated with gum arabic) | 24% |
| Example 1 Nougat structure Nystatin (coated with gum arabic) | 76% |

EXAMPLE 2

Chewing gum containing freely releasable particles of dicalcium phosphate coated with gum arabic having the composition set out below is prepared as follows.

|  | Example 2 Parts by Weight |
|---|---|
| Gum base | 17 |
| Sugar | 66 |
| Sorbitol syrup (68-72% sorbitol solids) | 11 |
| Malto-dextrin | 4 |
| Peppermint oil | 1 |
| Yelkin (Lecithin) | 0.2 |
| Peppermint (Spray dried flavor) | 0.5 |
| Dicalcium phosphate (coated with gum arabic) | 7.5 |

In the Example 2 composition, the weight ratio of dicalcium phosphate to gum arabic is 75:25.

Particles of dicalcium phosphate coated with gum arabic are prepared by simply mixing particles of dicalcium phosphate (average size of 200 mesh) into a 25% aqueous solution of gun arabic to form a suspension. The suspension is spray dried to produce the dicalcium phosphate particles coated with gum arabic.

The gum base is added to a steam jacketed kettle equipped with a sigma blade mixer. The temperature of the kettle is maintained at about 180° F. to 200° F. About one half of the sugar is thoroughly mixed into the melted gum base (while the gum base is folding well) for about 3 minutes to disperse the sugar throughout the continuous mass of gum base. The sugar is thereby trapped in or otherwise protected by the gum base. The liquid flavor is added and mixed for 1 minute. The remaining sugar is added with mixing for about 2 minutes thereby causing the mass to be torn into discrete pieces. Maltrin M100 (malto-dextrin) and liquid sorbitol are added to bring the mass together and mixed for about 2 minutes. At this point discrete pieces of gum base with trapped sugar are suspended in a water-soluble matrix of sorbitol liquid, malto-dextrin and sugar. Into this water-soluble phase is added the dicalcium phosphate sealed in gum arabic and mixed until a homogeneous dispersion is achieved.

The homogeneous dispersion is allowed to cool and is then sheeted, scored and cut into sticks (2.8 g each) and each containing 7.5% dicalcium phosphate.

As a Control D, chewing gum is prepared as described above except that the dicalcium phosphate present in the chewing gum is uncoated.

the calcium content is determined in the ash using atomic absorption analysis.

Five sticks of each gum are given to five people and these are asked to chew the gum for five minutes. The boluses are collected, pooled, ashed and calcium content is determined. This procedure is repeated and the panel is asked to chew the gums for ten minutes, and the calcium content of the boluses is determined.

The calcium extraction from each of the gums as a function of chewing time is summarized in Table II.

TABLE II

| | Loss of Calcium During Chewing of Gums Containing Dicalcium Phosphate | | | | | | | |
|---|---|---|---|---|---|---|---|---|
| | Time of Chewing (minutes) | Ex. 2 | Control D | Control E | Control F | Control G | Control H | Control I |
| Percent Calcium | 0 | 0 | 0 | 0 | 0 | 0 | 0 | 0 |
| Extracted | 5 | 52 | 18 | 40 | 5.9 | 16.3 | 33 | 33.7 |
| | 10 | — | — | — | 7.8 | 32.4 | 37.5 | 33.7 |
| | 15 | 66 | 28 | 50 | — | — | — | — |
| | 30 | 81 | 50 | 68 | 16.2 | 39.3 | 44.4 | 40.4 |

Ex. 2 - coated dicalcium phosphate (3 parts of dical to 1 part of gum arabic) added at end of sugar mix - discontinuous structure
Control D - uncoated dicalcium phosphate - added at end of sugar mix - discontinuous structure
Control E - sugar coated dicalcium phosphate added at end of sugar mix - discontinuous structure
Control F - uncoated dicalcium phosphate - added in base-syrup mix
Control G - coated dicalcium phosphate (4 parts dicalcium phosphate to 1 part gum arabic) ⎫ added in
Control H - coated dicalcium phosphate (3 parts dicalcium phosphate to 1 part gum arabic) ⎬ base-syrup
Control I - coated dicalcium phosphate (2.33 parts dicalcium phosphate to 1 part gum arabic) ⎭ mix As a Control E, chewing gum is prepared as described above except that the dicalcium phosphate present in the chewing gum is agglomerated with sugar in accordance with the technique described by Bilotti in U.S. Pat. No. 3,011,949.

Controls F, G, H and I chewing gums having the following composition are prepared as described below.

| | Controls F, G, H and I Parts by Weight |
|---|---|
| Gum base | 22 |
| Sugar | 50 |
| Corn syrup | 17 |
| Sorbitol | 10 |
| Peppermint oil | 1 |
| Yelkin (Lecithin) | 0.2 |
| Peppermint (Spray dried) | 0.5 |

In the Control F formulation 7.5% of uncoated dicalcium phosphate is present.

In the Control G, H and I formulations 7.5% of actual dicalcium phosphate which has been previously coated with gum arabic as described above in the following ratios (dicalcium phosphate:gum arabic 80:20 (Control G), 75:25 (Control H) and 2.33:1 (Control I)) is present.

The Controls F, G, H and I formulations are prepared as follows.

The gum base is melted and mixed with lecithin, corn syrup and the dicalcium phosphate (coated with gum arabic in the case of Controls G, H and I and uncoated in the case of Control F) for 5 minutes.

The resulting gum is cooled, sheeted, scored and cut into sticks (2.8 g each) and each containing 210 mg dicalcium phosphate.

The Example 2 and Controls D, E, F, G, H and I chewing gums are tested for dicalcium phosphate release as follows.

Samples of each of the chewing gums are submitted for calcium analysis. The chewing gums are ashed and The data indicate that:

The Control gums (D, E, F, G, H and I) release between 6 and 40% of the dicalcium phosphate during the first 5 minutes of chewing, 8 to 50% after 10-15 minutes of chewing, and 16 to 68% after 30 minutes of chewing. No significant increase in dicalcium phosphate release is noted by increasing the chewing time to 10 minutes.

The Example 2 gum containing dicalcium phosphate coated with gum arabic and prepared in accordance with the invention releases around 52% of the dicalcium phosphate after 5 minutes of chewing, 66% after 15 minutes of chewing and 81% after 30 minutes of chewing. These results are surprising and unexpectedly high as compared to the Control D, E, F, G, H and I gums. The data also indicate that increased release is obtained due to the coating of gum arabic as well as the structure of the gum itself.

EXAMPLE 3

Chewing gum containing freely releasable particles of magnesium hydroxide coated with gum arabic having the composition set out below is prepared as described in Example 1 except that particles of magnesium hydroxide coated with gum arabic are employed in place of nystatin.

| | Parts by Weight |
|---|---|
| Gum base | 17 |
| Sugar | 66 |
| Sorbitol syrup (68-72% sorbitol solids) | 11 |
| Malto-dextrin | 4 |
| Magnesium hydroxide coated with gum arabic (75:25) | 5 |
| Peppermint oil | 1 |
| Yelkin (Lecithin) | 0.2 |
| Peppermint (Spray Dried) | 0.5 |

As a Control J, chewing gum is prepared by conventional techniques as described with respect to Controls F through I in Example 2. Control J includes the gum arabic coated magnesium hydroxide.

Rates of extraction of the gum arabic coated magnesium hydroxide from the two chewing gums Control J—conventional mix and discontinuous mix—Example 3 are determined by a Soxhlet extraction and determination of magnesium hydroxide in the resultant extractants at various time intervals. These results are listed below in Table III.

TABLE III

Soxhlet Extraction of Chewing Gums Containing Gum Arabic Coated Magnesium Hydroxide

| | % Mg(OH)$_2$ Released | |
|---|---|---|
| Time (Hours) | Control J Conventional Mix | Example 3 Discontinuous Mix |
| 2 | 12.2 | 13.0 |
| 5 | 14.8 | 23.5 |
| 17 | 20.1 | 32.8 |
| 24 | 30.0 | 45.4 |
| 30 | 32.0 | 52.0 |
| 41 | 40.2 | — |
| 44 | — | 59.7 |
| 48 | 55.1 | 97.4 |

The results obtained show that the Example 3 gum releases magnesium hydroxide at a substantially faster rate than the Control J gum.

In view of the above results, it is clearly seen that both the unique structure of the chewing gum (Example 3) and the presence of the gum arabic coating greatly contribute to the release of the magnesium hydroxide from the chewing gum.

From the above, the following conclusions are apparent:

A nougat (discontinuous) structured chewing gum will release finely divided water insoluble materials more effectively than normal structured chewing gum.

A nougat structured chewing gum will release finely divided water insoluble material which has been previously treated with gum arabic faster than uncoated material is released, and will continue to release the material to near extinction.

A normal structured chewing gum will release finely divided water insoluble material which has been previously treated with gum arabic more effectively than untreated material but does not approach extinction.

What is claimed is:

1. A chewing gum capable of releasing finely divided water-insoluble therapeutic materials therefrom comprising a water-soluble phase comprised of softener, a finely divided water-insoluble therapeutic material coated with a water-soluble coating agent to facilitate release of said therapeutic material and prevent resorption back into the gum base, wherein said coating agent is gum arabic, a dextrin, gum tragacanth, gelatin, pectin, carboxymethyl cellulose, alginate, or other hydrocolloid or mixtures thereof, and a relatively water-insoluble phase consisting essentially of a plurality of separate and distinct masses suspended in and dispersed throughout the water-soluble phase, each of said masses comprising gum base, the water-soluble phase releasing said therapeutic material upon chewing.

2. The chewing gum as defined in claim 1 wherein said coating agent is gum arabic.

3. The chewing gum as defined in claim 1 wherein said coating agent is a dextrin, gum tragacanth, gelatin, pectin, carboxymethyl cellulose, alginate, or other hydrocolloid or mixtures thereof.

4. The chewing gum as defined in claim 1 wherein said coating agent is employed in a weight ratio of the therapeutic material of within the range of from about 1:4 to about 1:2.

5. The chewing gum as defined in claim 1 wherein said therapeutic material is dicalcium phosphate, magnesium hydroxide, calcium carbonate, aluminum hydroxide, nystatin, fat-soluble vitamins, antibiotics, propranolol, nadolol, or other medicaments.

6. The chewing gum as defined in claim 1 wherein said therapeutic material is dicalcium phosphate.

7. The chewing gum as defined in claim 1 wherein said therapeutic material is an antacid selected from the group consisting of magnesium hydroxide, calcium carbonate, aluminum hydroxide, magnesium carbonate and magnesium trisilicate.

8. The chewing gum as defined in claim 1 wherein said therapeutic material is an antibiotic selected from the group consisting of nystatin, amphotericin B and econazole.

9. The chewing gum as defined in claim 5 wherein said therapeutic material is propranolol or nadolol.

10. The chewing gum as defined in claim 1 further including a first sweetener in particulate form dispersed throughout the softener in said water soluble phase.

11. The chewing gum as defined in claim 10 wherein said first sweetener comprises a sugar, a sugar alcohol or mixtures thereof, and said second sweetener comprises a sugar or sugar alcohol or mixtures thereof.

12. The chewing gum as defined in claim 10, wherein said softener comprises sorbitol syrup, maltitol syrup, xylitol, corn syrup, hydrogenated starch hydrolysate or mixtures thereof.

13. The chewing gum as defined in claim 1 further including particles of a second sweetener enveloped by said gum base masses.

14. The chewing gum as defined in claim 13 wherein said second sweetener is sucrose, xylitol, mannitol, sorbitol, fructose syrup, glucose, glycyrrhizin, monoammonium salt of glycyrrhizin, calcium salt of glycyrrhizin, mono-, di- or trisodium salt of glycyrrhizin, mono-, di- or tripotassium salt of glycyrrhizin, calcium saccharin, sodium saccharin, ammonium saccharin, dihydrochalcones, neohesperidin dihydrochalcone, aspartame, Acesulfame-K, cyclamate salts, *Stevia rebaudiana, Richardella dulcifica, Dioscoreophyllum cumminsii*, and mixtures thereof.

15. The chewing gum as defined in claim 1 wherein said softener is sorbitol syrup.

16. The chewing gum as defined in claim 1 wherein said gum base is present in an amount within the range of from about 12 to about 25% by weight of the chewing gum.

17. The chewing gum as defined in claim 1 wherein said first sweetener is sorbitol powder, said softener is sorbitol syrup, and said second sweetener is mannitol, sorbitol or mixtures thereof.

18. The chewing gum as defined in claim 1 wherein said first sweetener is sucrose, said softener is sorbitol syrup and said second sweetener is sucrose.

19. The chewing gum as defined in claim 1 wherein said chewing gum is a sugarless gum and said water-soluble phase comprises from about 50 to about 92% by weight of the chewing gum, and said water-insoluble phase comprises from about 8 to about 50% by weight of the chewing gum.

20. A method for forming a chewing gum as defined in claim 1 which comprises interdispersing in melted gum base particles of a second sweetener to form a continuous phase, and thereafter mixing the continuous phase with a first sweetener causing the continuous phase to be torn into discrete masses of gum base enveloping said particles of second sweetener, mixing aqueous softener with the mixture of said discrete masses and first sweetener, and mixing said therapeutic material with said mixture of aqueous softener, said discrete masses and first sweetener to form a chewing gum which is smooth and continuous.

21. The method as defined in claim 20 wherein said therapeutic material is coated with gum arabic.

22. The chewing gum as defined in claim 1 having a short nougat-like discontinuous structure which is easily torn apart.

* * * * *

UNITED STATES PATENT AND TRADEMARK OFFICE
CERTIFICATE OF CORRECTION

PATENT NO. : 4,238,475

DATED : December 9, 1980

INVENTOR(S) : Frank Witzel et al.

It is certified that error appears in the above-identified patent and that said Letters Patent are hereby corrected as shown below:

On the Abstract page, first line of the title, "CUM" should read --GUM--.
On the Abstract page, second column, line 14, "suchas" should read --such as--.
Column 1, line 1, "CUM" should read --GUM--.
Column 5, line 67, "glactose" should read --galactose--.

Signed and Sealed this

Tenth Day of March 1981

[SEAL]

Attest:

RENE D. TEGTMEYER

*Attesting Officer*     *Acting Commissioner of Patents and Trademarks*